(12) United States Patent
Ye et al.

(10) Patent No.: US 11,085,862 B2
(45) Date of Patent: Aug. 10, 2021

(54) NATURAL GAS HYDRATE-BEARING SEDIMENT INTERGRANULAR MICRO-FORCE TESTING DEVICE AND TESTING METHOD THEREOF

(71) Applicants: Guangzhou Marine Geological Survey, Guangzhou (CN); China University of Geosciences(Wuhan), Wuhan (CN)

(72) Inventors: Jianliang Ye, Guangzhou (CN); Xuwen Qin, Guangzhou (CN); Fulong Ning, Guangzhou (CN); Yanjiang Yu, Guangzhou (CN); Qiang Luo, Guangzhou (CN); Tinghui Wan, Guangzhou (CN); Zhichao Liu, Guangzhou (CN); Haoxian Shi, Guangzhou (CN); Xiangyu Fang, Guangzhou (CN); Qiuping Lu, Guangzhou (CN); Dongdong Wang, Guangzhou (CN)

(73) Assignees: Guangzhou Marine Geological Survey, Guangzhou (CN); China University of Geosciences (Wuhan), Wuhan (CN)

( * ) Notice: Subject to any disclaimer, the term of this patent is extended or adjusted under 35 U.S.C. 154(b) by 186 days.

(21) Appl. No.: 16/531,672

(22) Filed: Aug. 5, 2019

(65) Prior Publication Data

US 2020/0072734 A1 Mar. 5, 2020

(30) Foreign Application Priority Data

Aug. 28, 2018 (CN) .......................... 201810985252.2

(51) Int. Cl.
*G01N 15/00* (2006.01)
*G01N 33/24* (2006.01)
(Continued)

(52) U.S. Cl.
CPC ............. *G01N 15/00* (2013.01); *G01N 15/04* (2013.01); *G01N 19/02* (2013.01); *G01N 33/24* (2013.01)

(58) Field of Classification Search
CPC ........ G01N 19/02; G01N 33/24; G01N 19/04; G01N 15/00; G01N 15/04
See application file for complete search history.

(56) References Cited

U.S. PATENT DOCUMENTS

2016/0305205 A1* 10/2016 Li ......................... E21B 47/007
2016/0357888 A1* 12/2016 Li ............................ E21B 43/34

FOREIGN PATENT DOCUMENTS

CN 1176741 * 11/2004 .............. B41J 19/00
CN 1752734 A 3/2006
(Continued)

*Primary Examiner* — Benjamin R Schmitt
(74) *Attorney, Agent, or Firm* — Muncy, Geissler, Olds & Lowe, P.C.

(57) ABSTRACT

The present invention discloses a natural gas hydrate-bearing sediment intergranular micro-force testing device and a testing method thereof. The testing device comprises: a high pressure reactor, a natural gas cylinder, a natural gas buffer tank, a condensate circulation device, a water source and a gas-liquid saturated tank, wherein a gas inlet of the natural gas buffer tank communicates with the natural gas cylinder through a first pipeline, a gas outlet of the natural gas buffer tank communicates with a gas inlet of the high pressure reactor through a second pipeline, a water inlet of the high pressure reactor communicates with a water outlet of the gas-liquid saturated tank through a third pipeline, a water inlet of the gas-liquid saturated tank communicates with the water source through a fourth pipeline, the gas outlet of the natural gas buffer tank communicates with the fourth pipeline through a fifth pipeline.

9 Claims, 2 Drawing Sheets

(51) Int. Cl.
  *G01N 19/02* (2006.01)
  *G01N 15/04* (2006.01)

(56) References Cited

FOREIGN PATENT DOCUMENTS

| CN | 105301200 | * | 2/2016 | ............. G01N 33/00 |
| CN | 207439900 U | | 6/2018 | |

* cited by examiner

NATURAL GAS HYDRATE-BEARING SEDIMENT INTERGRANULAR MICRO-FORCE TESTING DEVICE AND TESTING METHOD THEREOF

TECHNICAL FIELD

The present invention relates to the field of natural gas hydrates, and in particular to a natural gas hydrate-bearing sediment intergranular micro-force testing device.

BACKGROUND

Natural gas hydrates in nature are considered to be new sources of potential energy in the future, but they face the risk of sand production and well bury in the process of exploration and development of natural gas hydrates. Therefore, it is necessary to study the reservoir sand production mechanism and its laws in depth, and then propose sand control measures and optimize the mining regulations. The origin of sand production in hydrate reservoirs is still the cause of mechanics. The interaction between sediment particles and between sediment particles and hydrate particles is one of the key factors for sand migration. Studying and evaluating the interaction between sediment particles and between sediment particles and hydrate particles can provide mesoscopic parameters for numerical simulation of sand production based on discrete medium theory, which is important to accurately reveal the sand production mechanism of hydrate reservoirs, master the sand production law and guide the design of sediment prevention and control to achieve long-term efficient mining.

Existing hydrate-bearing sediment intergranular micro-force testing devices are based on the oil and gas phase environments in oil and gas transport pipelines, but natural gas hydrate-bearing sediment in nature are often filled with hydrates and water in skeletal pores or fractures. Therefore, it is necessary to test the cohesion and friction between hydrate particles and sand or clay particles in the aqueous phase, the gas phase and the gas-liquid mixed environment. However, there are no related devices and methods to evaluate the hydrate-bearing sediment intergranular action force.

SUMMARY

In order to overcome the deficiencies of the prior art, a first object of the present invention is to provide a natural gas hydrate-bearing sediment intergranular micro-force testing device capable of testing the cohesion and friction between hydrate particles and sand or clay particles in an aqueous phase, a gas phase, and a gas-liquid mixed environment.

A second object of the present invention is to provide a natural gas hydrate-bearing sediment intergranular micro-force testing method, which can test the cohesion and friction between hydrate particles and sand or clay particles in an aqueous phase, a gas phase and a gas-liquid mixed environment.

In order to achieve the first object, the technical solution adopted by some example embodiments are as follows:

A natural gas hydrate-bearing sediment intergranular micro-force testing device, comprising: a high pressure reactor, a natural gas cylinder, a natural gas buffer tank, a condensate circulation device, a water source and a gas-liquid saturated tank, wherein a gas inlet of the natural gas buffer tank communicates with the natural gas cylinder through a first pipeline, a gas outlet of the natural gas buffer tank communicates with a gas inlet of the high pressure reactor through a second pipeline, a water inlet of the high pressure reactor communicates with a water outlet of the gas-liquid saturated tank through a third pipeline, a water inlet of the gas-liquid saturated tank communicates with the water source through a fourth pipeline, the gas outlet of the natural gas buffer tank communicates with the fourth pipeline through a fifth pipeline, the high pressure reactor is provided with a cantilever testing module and a granule fixing module, the cantilever testing module includes a cantilever, a tension sensor and a nano-displacement platform, one end of the tension sensor is connected to the nano-displacement platform, and the other end is connected to the cantilever; a first temperature sensor and a first pressure sensor are disposed at the gas inlet of the high-pressure reactor, a second temperature sensor and a second pressure sensor are disposed at the water inlet of the high pressure reactor, the high pressure reactor is provided with a visible window, one side of the visible window is provided with a stereo microscope, an outlet of the condensate circulation device is connected with a first cooling water outlet pipeline and a second cooling water outlet pipeline, the first cooling water outlet pipeline and the second cooling water outlet pipeline are respectively wound around an outer wall of the high pressure reactor, and a water outlet of the condensate circulation device communicates with the gas-liquid saturated tank.

Furthermore, the natural gas hydrate-bearing sediment intergranular micro-force testing device further comprises a controller, wherein the tension sensor and the nano-displacement platform are respectively connected to the controller, the stereo microscope is connected to the controller, the first temperature sensor and the first pressure sensor are respectively connected to the controller, and the second temperature sensor and the second pressure sensor are respectively connected to the controller.

Furthermore, the first pipeline is provided with a first globe valve, a first pressure gauge and a second globe valve.

Furthermore, the second pipeline is provided with a second pressure gauge, a third globe valve, a fourth globe valve and a first check valve.

Furthermore, the third pipeline is provided with a fifth globe valve and a second check valve, the fourth pipeline is provided with a sixth globe valve, and the fifth pipeline is provided with a seventh globe valve.

Furthermore, the gas outlet of the high-pressure reactor is provided with an eighth globe valve, and the water outlet of the high pressure reactor is provided with a ninth globe valve.

Furthermore, the visible window is a visible transparent sapphire window.

In order to achieve the second object, the technical solution adopted by some example embodiments are as follows:

A natural gas hydrate-bearing sediment intergranular micro-force testing method, comprising a natural gas hydrate-bearing sediment intergranular micro-force testing device according to any one of claims 1 to 7, comprising the steps of:

S1, dropping a drop of water on the cantilever of the cantilever testing module in the high pressure reactor, and fixing sediment particles to be tested on the granule fixing module;

S2, adjusting the natural gas cylinder and the natural gas buffer tank to a pressure required for testing, the natural gas passing through the fourth globe valve and the first check valve in an upper part of the high-pressure reactor to enter the high pressure reactor;

S3, turning on the condensate circulation device to cool the high pressure reactor and lower the temperature in the high pressure reaction reactor to a test temperature;

S4, after the water droplets on the cantilever form a hydrate, adjusting the pressure of the water source, and the water being saturated with the natural gas from the natural gas buffer tank through the gas-liquid saturated tank and precooled near a hydrate-bearing sediment temperature to enter the high pressure reactor, so that the liquid in the high pressure reactor is raised to a required liquid level for testing; and S5, performing test by the stereo microscope in cooperation with the cantilever of the cantilever testing module.

Furthermore, after being pre-cooled, the water enters the high pressure reactor through the fifth globe valve and the second check valve in a lower part of the high-pressure reactor.

Compared with the prior art, the present invention has the beneficial effects that the high pressure reactor is provided with a cantilever testing module and a granule fixing module, the cantilever testing module includes a cantilever, a tension sensor and a nano-displacement platform, one end of the tension sensor is connected to the nano-displacement platform, and the other end is connected to the cantilever; a first temperature sensor and a first pressure sensor are disposed at the gas inlet of the high-pressure reactor, a second temperature sensor and a second pressure sensor are disposed at the water inlet of the high pressure reactor, the high pressure reactor is provided with a visible window, one side of the visible window is provided with a stereo microscope, an outlet of the condensate circulation device is connected with a first cooling water outlet pipeline and a second cooling water outlet pipeline, the first cooling water outlet pipeline and the second cooling water outlet pipeline are respectively wound around an outer wall of the high pressure reactor, and a water outlet of the condensate circulation device communicates with the gas-liquid saturated tank; the present invention can simulate a natural environment in which the water, natural gas hydrate and sediment particles of the natural gas hydrate-bearing sediment coexist, and is provided with a tension sensor and a nano-displacement platform, which can record the force and displacement of the cantilever testing module in the vertical and horizontal directions, and test cohesion and friction between hydrate particles and sediment particles in the gas phase, the aqueous phase and the gas-liquid mixed environment under corresponding temperature and pressure conditions, is provided with a first temperature sensing and a first pressure sensor, which can measure the temperature and pressure of the gas phase environment in the upper part of the high pressure reactor, and is also provided with a second temperature sensor and a second pressure sensor, which can measure the temperature and pressure of the liquid phase environment in the lower part of the high pressure reactor.

BRIEF DESCRIPTION OF THE DRAWINGS

The specific embodiments of the present invention are further described in detail below with reference to the accompanying drawings, in which.

Figure 1:
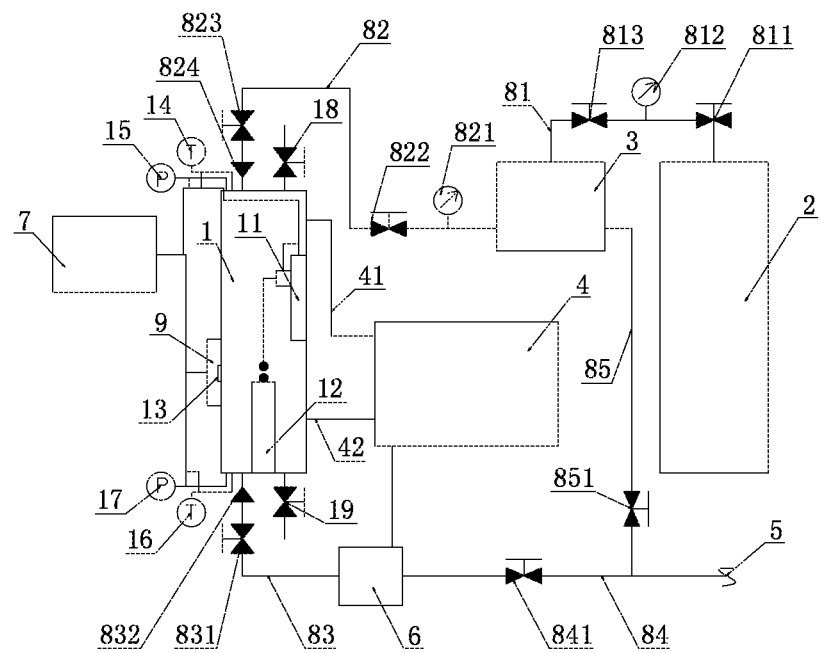
FIG. 1 is a schematic view of the structure of the present invention.

In the figure: 1—high pressure reactor, 2—natural gas cylinder, 3—natural gas buffer tank, 4—condensate circulation device, 5—water source, 6—gas-liquid saturated tank, 7—controller, 9—stereo microscope, 11—cantilever testing module, 12—granule fixing module, 13—visual window, 14—first temperature sensor, 15—first pressure sensor, 16—second temperature sensor, 17—second pressure sensor, 18—eighth globe valve, 19—ninth globe valve, 41—first cooling water outlet pipeline, 42—second cooling water outlet pipeline, 81—first pipeline, 82—second pipeline, 83—third pipeline, 84—fourth pipeline, 85—fifth pipeline, 111—cantilever, 112—tension sensor, 113—nano-displacement platform, 811—first globe valve, 812—first pressure gauge, 813—second globe valve, 821—second pressure gauge, 822—third globe valve, 823—fourth globe valve, 824—first check valve, 831—fifth globe valve, 832—second check valve, 841—sixth globe valve, 851—seventh globe valve.

DETAILED DESCRIPTION

The preferred embodiments of the present invention are described in conjunction with the accompanying drawings, and the preferred embodiments of the present invention are intended to illustrate and explain the present invention.

In the description of the present invention, it should be noted that the orientation or positional relationship indicated by the terms "center", "upper", "lower", "left", "right", "vertical", "horizontal", "inside", "outside", etc. is based on the orientation or positional relationship shown in the drawings, and is merely for the convenience of describing the present invention and simplifying the description, and does not indicate or imply that the device or component referred to has a specific orientation or is constructed and operated in a specific orientation and therefore shall not to be construed as limiting the present invention. Moreover, the terms "first," "second," and "third" are used for descriptive purposes only and are not to be construed as indicating or implying relative importance.

In the description of the present invention, unless otherwise explicitly specified and defined, it should be noted that the terms "installation", "connected with", and "connected to" are to be understood broadly, and may be, for example, fixedly connected or detachably connected, or integrally connected; may be mechanically connected or electrically connected; may be directly connected, or indirectly connected through an intermediate medium, and may be the internal communication of the two components. The specific meaning of the above terms in the present invention can be understood in a specific case by those skilled in the art.

Figure 2:
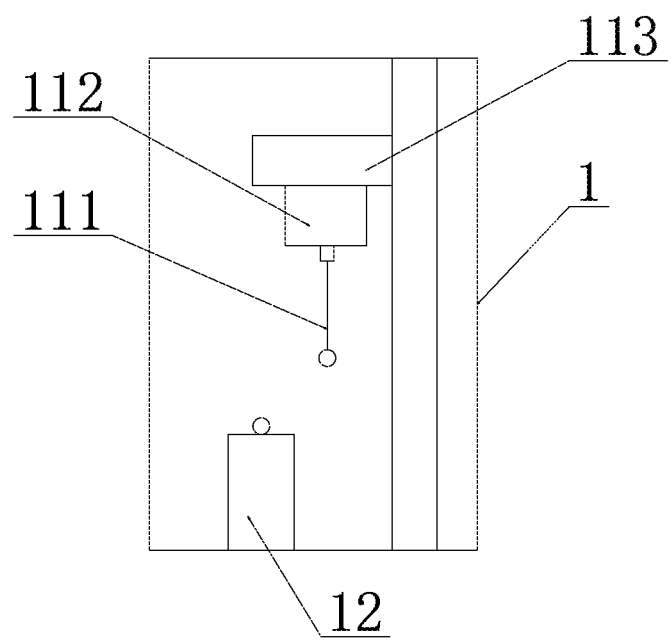
FIG. 2 is a schematic structural view of a high pressure reactor, a cantilever testing module and a granule fixing module according to the present invention.

As shown in FIGS. 1-2, a natural gas hydrate-bearing sediment intergranular micro-force testing device includes a high pressure reactor 1, a natural gas cylinder 2, a natural gas buffer tank 3, a condensate circulation device 4, a water source 5, a gas-liquid saturated tank 6 and a controller 7. A gas inlet of the natural gas buffer tank 3 communicates with the natural gas cylinder 2 through a first pipeline 81. A gas outlet of the natural gas buffer tank 3 communicates with a gas inlet of the high-pressure reactor 1 through a second pipeline 82. A water inlet of the high pressure reactor communicates with a water outlet of the gas-liquid saturated tank 6 through a third pipeline 83. A water inlet of the gas-liquid saturated tank 6 communicates with the water source 5 through a fourth pipeline 84. The gas outlet of the natural gas buffer tank 3 communicates with the fourth pipeline 84 through a fifth pipeline 85. The high pressure reactor 1 is provided with a cantilever testing module 11 and a granule fixing module 12. The cantilever testing module 11 includes a cantilever 111, a tension sensor 112, and a nano-displacement platform 113. One end of the tension sensor 112 is connected to the nano-displacement platform 113, and the other end is connected to the cantilever 111. A visual window 13 is provided on the high pressure reactor 1. One side of the visual window 13 is provided with a stereo microscope 9. The stereo microscope 9 is connected to the controller 7.

Specifically, the tension sensor 112 and the nano-displacement platform 113 are respectively connected to the controller 7. The nano-displacement platform 113 is used for testing the displacement of the cantilever testing module 11 in the vertical direction and the horizontal direction. The tension sensor 112 is used for testing the cohesion and friction between hydrate particles and sediment particles under microscopic scale. Preferably, the nano-displacement platform 113 selects the L series linear platform of Shanghai PI Nano-displacement Technology Co., Ltd. The specific model of the nano-displacement platform 113 needs to be determined according to the accuracy of the bearing capacity and the moving speed.

Specifically, a first cooling water outlet pipeline 41 and a second cooling water outlet pipeline 42 are connected to an outlet of the condensate circulation device 4. The first cooling water outlet pipeline 41 and the second cooling water outlet pipeline. 42 are respectively wound around an outer wall of the high pressure reactor 1. A water outlet of the condensate circulation device 4 communicates with the gas-liquid saturated tank 6. The first cooling water outlet pipeline 41 and the second cooling water outlet pipeline 42 are respectively wound on the outer wall of the high pressure reactor 1. The high pressure reactor 1 can be cooled due to the good cooling ability of the condensate circulation device 4 so that the pressure of the high pressure reactor 1 is rapidly lowered. The condensate circulation device 4 communicates with the gas-liquid saturated tank 6 through a pipeline, and injects cold water into the gas-liquid saturated tank 6 to cool down.

Specifically, the gas-liquid saturated tank 6 is disposed in the natural gas hydrate-bearing sediment intergranular micro-force testing device. The gas-liquid saturated tank 6 can adjust the liquid level of the saturated water so that the natural gas hydrate particles and the sediment particles are tested above or below the liquid level of the saturated water environment. The gas-liquid saturated tank 6 functions similarly to a pressure vessel. When water and gas enter the gas-liquid saturated tank 6, the water and gas are saturated under pressure. When the gas pressure cannot continue to increase and is maintained at a certain value, the water has been saturated with this portion of gas. Then the fifth globe valve 831 is opened to pass this portion of saturated solution into the high pressure reactor 1 to simulate the formation saturated water environment at the time of gas hydrate-bearing sediment.

Specifically, both the cantilever testing module 11 and the granule fixing module 12 are fixed in the high pressure reactor 1. The cantilever testing module 11 is disposed at an upper part of the high pressure reactor 1 to avoid contact with water in a lower part of the high pressure reactor 1. When tested by the natural gas hydrate-bearing sediment intergranular micro-force testing device, the cantilever testing module 11 will produce horizontal and vertical movement of the cantilever 111 to allow the hydrate particles and the sediment particles to be tested for cohesion and friction.

Specifically, the hydrate particles on the cantilever 111 move in the downward and horizontal directions to contact with the sediment particles under the movement of the nano-displacement platform 113. Then the cantilever 111 is pulled upward by the nano-displacement platform 113. At this time, the maximum value of the force data recorded by the tension sensor 112 is cohesion. When measuring the friction, a rectangular piece made of the sediment particles on the granule fixing module 1 is in contact with the hydrate particles. The cantilever 111 is pulled upward by the nano-displacement platform 113. At this time, the data recorded by the tension sensor 112 is friction.

Specifically, a first temperature sensor 14 and a first pressure sensor 15 are disposed at the gas inlet of the high pressure reactor 1. The first temperature sensor 14 and the first pressure sensor 15 are respectively connected to the controller 7. A second temperature sensor 16 and a second pressure sensor 17 are disposed at the water inlet of the high pressure reactor 1. The first temperature sensor 14 and the first pressure sensor 15 are respectively connected to the controller 7. The first temperature sensor 14 is used to measure the temperature of the gas phase environment in the upper part of the high pressure reactor 1. The first pressure sensor 15 is used to measure the pressure of the gas phase environment in the upper part of the high pressure reactor 1. The second temperature sensor 16 is used for measuring the temperature of the liquid phase environment in the lower part of the high pressure reactor 1. The second pressure sensor 17 is used to measure the pressure of the liquid phase environment in the lower part of the high pressure reactor 1.

Specifically, the controller 7 is configured to receive signals and process data, receive image data from the stereo microscope 9 and data from the first temperature sensor 14, the second temperature sensor 16, the first pressure sensor 15, the second pressure sensor 17, the nano-displacement platform 113 and the tension sensor 112 such that the vertical displacement and horizontal displacement data of the cantilever testing module 11 and the cohesion and friction between the hydrate particles and the sediment particles are obtained.

Specifically, the first pipeline 81 is provided with a first globe valve 811, a first pressure gauge 812 and a second globe valve 813. Preferably, the first pipeline 81 is sequentially provided with a first globe valve 811, a first pressure gauge 812, and a second globe valve 813 from the natural gas cylinder 2 to the natural gas buffer tank 3.

Specifically, the second pipeline 82 is provided with a second pressure gauge 821, a third globe valve 822, a fourth globe valve 823 and a first check valve 824. Preferably, the second pipeline 82 is sequentially provided with a second pressure gauge 821, a third globe valve 822, a fourth globe valve 823, and a first check valve 824 from the natural gas buffer tank 3 to the high pressure reactor 1.

Specifically, the third pipeline 83 is provided with a fifth globe valve 831 and a second check valve 832. The fourth pipeline 84 is provided with a sixth globe valve 841. The fifth pipeline 85 is provided with a seventh globe valve 851.

Specifically, an eighth globe valve 18 is disposed at the gas outlet of the high pressure reactor 1. A ninth globe valve 19 is disposed at the water outlet of the high pressure reactor 1.

Specifically, the visible window 13 is a visible transparent sapphire window. The visible transparent sapphire window can cooperate with the stereo microscope 9 to observe the particles under test in the high pressure reactor 1 from a better perspective.

As shown in FIG. 1, the bottom of the high pressure reactor 1 is provided with a fifth globe valve 831. The fifth globe valve 831 is opened when the test is performed, so that the water level of the saturated water in the lower part of the high pressure reactor 1 can be lower or higher than the height of the sediment particles, which allows the high pressure reactor 1 to simulate the micromechanical testing of the groundwater saturated natural gas environment. After the end of the test, the ninth globe valve 19 at the bottom of the high pressure reactor 1 is opened to drain the water from the high pressure reactor 1.

Specifically, the first globe valve 811, the second globe valve 813, the third globe valve 822, the fourth globe valve 823, the fifth globe valve 831, the sixth globe valve 841, the seventh globe valve 851, the eighth globe valve 18 and the ninth globe valve 19 can not only discharge the water and gas from the high pressure reactor 1 after the end of the test, but also can cooperate with the first check valve 824 and the second check valve 832 to adjust the pressure in the gas phase and the aqueous phase of the high pressure reactor 1 to reach the pressure required for the test.

A natural gas hydrate-bearing sediment intergranular micro-force testing method comprises the following steps.

In step S1, a drop of water is dropped on the cantilever 111 of the cantilever testing module 11 in the high pressure reactor 1, and sediment particles to be tested are fixed on the granule fixing module 12.

In step S2, the natural gas cylinder 2 and the natural gas buffer tank 3 are adjusted to a pressure required for testing, and the natural gas enters the high pressure reactor 1 through the fourth globe valve 823 and the first check valve 824 in the upper part of the high pressure reactor 1.

In step S3, the condensate circulation device 4 is turned on to cool the high pressure reactor 1, and the temperature in the high pressure reactor 1 is lowered to a test temperature.

In step S4, after the water droplets on the cantilever 111 form a hydrate, the pressure of the water source 5 is adjusted, and the water is saturated with the natural gas from the natural gas buffer tank 3 through the gas-liquid saturated tank 6 and precooled near a hydrate-bearing sediment temperature and then enter the high pressure reactor 1 through the fifth globe valve 831 and the second check valve 832 in the lower part of the high pressure reactor 1 so that the liquid of the high pressure reactor 1 rises to a required liquid level for testing.

In step S5, the test is performed by the stereo microscope 9 in cooperation with the cantilever 111 of the cantilever testing module 11.

Various other changes and modifications may be made by those skilled in the art in light of the above-described technical solutions and concepts, and all such changes and modifications are intended to fall within the scope of the appended claims.

What is claimed is:

1. A natural gas hydrate-bearing sediment intergranular micro-force testing device, comprising: a high pressure reactor, a natural gas cylinder, a natural gas buffer tank, a condensate circulation device, a water source and a gas-liquid saturated tank, wherein a gas inlet of the natural gas buffer tank communicates with the natural gas cylinder through a first pipeline, a gas outlet of the natural gas buffer tank communicates with a gas inlet of the high pressure reactor through a second pipeline, a water inlet of the high pressure reactor communicates with a water outlet of the gas-liquid saturated tank through a third pipeline, a water inlet of the gas-liquid saturated tank communicates with the water source through a fourth pipeline, the gas outlet of the natural gas buffer tank communicates with the fourth pipeline through a fifth pipeline, the high pressure reactor is provided with a cantilever testing module and a granule fixing module, the cantilever testing module includes a cantilever, a tension sensor and a nano-displacement platform, one end of the tension sensor is connected to the nano-displacement platform, and the other end is connected to the cantilever; a first temperature sensor and a first pressure sensor are disposed at the gas inlet of the high-pressure reactor, a second temperature sensor and a second pressure sensor are disposed at the water inlet of the high pressure reactor, the high pressure reactor is provided with a visible window, one side of the visible window is provided with a stereo microscope, an outlet of the condensate circulation device is connected with a first cooling water outlet pipeline and a second cooling water outlet pipeline, the first cooling water outlet pipeline and the second cooling water outlet pipeline are respectively wound around an outer wall of the high pressure reactor, and a water outlet of the condensate circulation device communicates with the gas-liquid saturated tank.

2. The natural gas hydrate-bearing sediment intergranular micro-force testing device according to claim 1, further comprising a controller, wherein the tension sensor and the nano-displacement platform are respectively connected to the controller, the stereo microscope is connected to the controller, the first temperature sensor and the first pressure sensor are respectively connected to the controller, and the second temperature sensor and the second pressure sensor are respectively connected to the controller.

3. The natural gas hydrate-bearing sediment intergranular micro-force testing device according to claim 1, wherein the first pipeline is provided with a first globe valve, a first pressure gauge and a second globe valve.

4. The natural gas hydrate-bearing sediment intergranular micro-force testing device according to claim 1, wherein the second pipeline is provided with a second pressure gauge, a third globe valve, a fourth globe valve and a first check valve.

5. The natural gas hydrate-bearing sediment intergranular micro-force testing device according to claim 1, wherein the third pipeline is provided with a fifth globe valve and a second check valve, the fourth pipeline is provided with a sixth globe valve, and the fifth pipeline is provided with a seventh globe valve.

6. The natural gas hydrate-bearing sediment intergranular micro-force testing device according to claim 1, wherein the gas outlet of the high-pressure reactor is provided with an eighth globe valve, and the water outlet of the high pressure reactor is provided with a ninth globe valve.

7. The natural gas hydrate-bearing sediment intergranular micro-force testing device according to claim 1, wherein the visible window is a visible transparent sapphire window.

8. A natural gas hydrate-bearing sediment intergranular micro-force testing method, comprising a natural gas hydrate-bearing sediment intergranular micro-force testing device according to claim 1, comprising the steps of:
   S1, dropping a drop of water on the cantilever of the cantilever testing module in the high pressure reactor, and fixing sediment particles to be tested on the granule fixing module;
   S2, adjusting the natural gas cylinder and the natural gas buffer tank to a pressure required for testing, the natural gas passing through the fourth globe valve and the first check valve in an upper part of the high-pressure reactor to enter the high pressure reactor;

S3, turning on the condensate circulation device to cool the high pressure reactor and lower the temperature in the high pressure reaction reactor to a test temperature;

S4, after the water droplets on the cantilever form a hydrate, adjusting the pressure of the water source, and the water being saturated with the natural gas from the natural gas buffer tank through the gas-liquid saturated tank and precooled near a hydrate-bearing sediment temperature to enter the high pressure reactor, so that the liquid in the high pressure reactor is raised to a required liquid level for testing; and S5, performing test by the stereo microscope in cooperation with the cantilever of the cantilever testing module.

9. The natural gas hydrate-bearing sediment intergranular micro-force testing method according to claim 8, wherein after being pre-cooled, the water enters the high pressure reactor through the fifth globe valve and the second check valve in a lower part of the high-pressure reactor.

* * * * *